(12) United States Patent
Farzin-Nia et al.

(10) Patent No.: US 6,315,558 B1
(45) Date of Patent: Nov. 13, 2001

(54) METHOD OF MANUFACTURING SUPERELASTIC ENDODONTIC FILES AND FILES MADE THEREFROM

(75) Inventors: Farrokh Farzin-Nia, Inglewood; William Otsen, Glendora, both of CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/426,598

(22) Filed: Oct. 26, 1999

Related U.S. Application Data

(62) Division of application No. 08/938,507, filed on Sep. 26, 1997, now Pat. No. 5,984,679.

(51) Int. Cl.[7] ............................................. A61C 5/02
(52) U.S. Cl. ............................................. 433/102
(58) Field of Search .................... 433/102, 224, 433/165, 166; 451/48

(56) References Cited

U.S. PATENT DOCUMENTS

| | | | |
|---|---|---|---|
| 4,443,193 | 4/1984 | Roane | 433/102 |
| 5,044,947 | 9/1991 | Sachdeva et al. | 433/20 |
| 5,106,298 | 4/1992 | Heath et al. | 433/102 |
| 5,125,838 | 6/1992 | Seigneurin | 433/102 |
| 5,302,129 | 4/1994 | Heath et al. | 433/224 |
| 5,429,501 | 7/1995 | Farzin-Nia et al. | 433/21 |
| 5,464,362 | * 11/1995 | Heath et al. | 433/102 X |
| 5,527,205 | 6/1996 | Heath et al. | 451/48 |
| 5,628,674 | 5/1997 | Heath et al. | 451/48 |
| 5,655,950 | 8/1997 | Heath et al | 451/48 |
| 5,752,825 | 5/1998 | Buchanan | 433/102 X |
| 5,762,541 | 6/1998 | Heath et al. | 433/102 X |
| 5,775,902 | * 7/1998 | Matsutani et al. | 433/102 |
| 5,902,106 | * 5/1999 | McSpadden | 433/102 |
| 5,941,760 | * 8/1999 | Heath et al. | 433/102 |
| 6,015,292 | * 1/2000 | Eurard et al. | 433/102 |

OTHER PUBLICATIONS

Harmeet Walia et al., *An Initial Investigation of the Bending and Torsional Properties of Nitinol Root Canal Files*, Journal of Endodontics, vol. 14, No. 7, Jul. 1988.

* cited by examiner

*Primary Examiner*—Nicholas D. Lucchesi
(74) *Attorney, Agent, or Firm*—Wood, Herron & Evans, L.L.P.

(57) ABSTRACT

A method of forming a superelastic endodontic file by grinding a superelastic wire to form a file blank, and rotating a first end of the blank while preventing rotation of a second end of the blank is disclosed. The file blank is maintained in the austenite phase until twisted to form a stress induced martensite which is plastically deformed by the twisting. A heat treatment step may be performed prior to twisting, during twisting or after twisting of the preform. The method disclosed allows for increased flexibility in the design of files including the production of a rhomboid superelastic file.

30 Claims, 3 Drawing Sheets

METHOD OF MANUFACTURING SUPERELASTIC ENDODONTIC FILES AND FILES MADE THEREFROM

This appln. is a Div. of Ser. No. 08/938,507 filed Sep. 26, 1997, U.S. Pat. No. 5,984,679.

BACKGROUND OF THE INVENTION

Previously known endodontic root canal files have been primarily made from carbon steel or stainless steel wire blanks which are ground to a desired size, taper and cross-sectional shape (for example, square, triangular or rhomboid). The wire blank is gripped on a first end while spring-loaded jaws secure the ground portion of the blank. The blank is then rotated from the gripped end while the jaws are moved axially away from that end. The jaws which secure the ground portion move along the ground wire blank, but do not allow the distal end of the blank to twist, thereby forming a twisted portion and helical flutes from the edges of the blank between the gripped end and the jaws. The cross-sectional shape, size and taper as well as the speed of twisting and spring force may be controlled to attain the desired properties in the final product. One such endodontic instrument is shown in U.S. Pat. No. 4,443,193, herein incorporated in its entirety by reference.

With the introduction of superelastic materials such as nickel titanium alloys, it has been recognized that superelastic endodontic files would provide more elastic flexibility in bending and torsion than the previous steel files. The paper, *An Initial Investigation of the Bending and Torsional Properties of Nitinol Root Canal Files,* Walia et al., *Journal of Endodontics,* Volume XIV, No. 7, July 1988, studied the feasibility of manufacturing superelastic nickel titanium root canal files and evaluated the bending and torsional properties of these instruments. In order to fabricate nickel titanium files the Walia article discloses the machining of the fluted structure of a K-type file directly on cylindrical wire blanks.

U.S. Pat. Nos. 5,464,362, 5,527,205 and 5,628,674 disclose the machining process used to grind the files disclosed in the Walia et al. article in which the fluted structure of the K-type file is ground directly on a cylindrical nickel titanium wire blank to create cutting edges at the apices. U.S. Pat. No. 5,464,362 provides a cylindrical rod of superelastic material having a diameter between 0.0024" and 0.062" which is translated axially, relative to a rotating grinding wheel, at an axial feed rate of between about 3 inches per minute and 8 inches per minute, with the preferred rate being not more than about 5 inches per minute. The rod is rotated about its longitudinal axis while it is translated relative to the wheel so that the wheel removes at least about 25% of the diameter of the rod at the point of maximum removal and forms at least one helical flute in the rod. In order to accomplish this grinding, the wheel is rotated at a surface speed of not more than about 3,000 surface feet per minute and preferably not more than about 2,200 surface feet per minute. The grinding wheel also has a grit size greater than about 200 grit and preferably greater than about 220 grit. If the file of the U.S. Pat. No. 5,464,362 patent is to have more than one helical flute, a first flute is ground, the rod is indexed about its longitudinal axis either by 180° (two flutes), or 120° (three flutes), and the grinding step is repeated.

SUMMARY OF THE INVENTION

In order to provide an endodontic file with a low modulus of elasticity which is more flexible in bending and torsion than conventional steel files and to overcome the problems with grinding disclosed in the Walia article and which the U.S. Pat. Nos. 5,464,362, 5,527,205 and 5,628,674 patents continue to have, a preground superelastic blank of a predetermined cross-sectional shape is twisted to provide helical flutes. In order to maintain its shape the file is maintained in the austenite phase until twisted. To maintain the file preform in the austenite phase the file is maintained above the austenite finish temperature Af prior to and during twisting. The material of the file is converted from the austenite phase to the martensite phase by the stress applied in twisting. This stress induced martensite is plastically deformed during twisting so that the fluted profile is retained after the twisting process is performed. Due to the pregrinding of the file preform it is possible to fabricate a superelastic file having myriad transverse cross-sections, including a rhomboid cross-sections, from a superelastic material.

DETAILED DESCRIPTION OF THE INVENTION

Superelastic materials are alloys which return to their original shape after substantial deformation. Superelastic alloys such as nickel titanium (NiTi) can withstand several times more strain than conventional materials, such as stainless steel, without becoming plastically deformed. Further, a superelastic material will generally recover approximately 6% after twisting at ambient temperature while a stainless steel will recover only 1–2% after twisting. Typically, superelastic alloys undergo a stress induced martensitic transformation which allows for shape memory properties. Shape memory and superelasticity are found in stoichiometric NiTi, near-equiatomic Ni-Ti, for example, 50.8 atomic percent Ti and 49.2 atomic percent Ni, Ni-Ti-Cu, Ni-Ti-Nb and Ni-Ti-Fe alloys as well as beta-phase titanium or other Ti based alloys. Examples of suitable nickel-titanium alloys in various stoichiometric ratios are disclosed in U.S. Pat. No. 5,044,947 (nickel-titanium-copper alloy) and U.S. patent applications Ser. Nos. 08/221,638 and 08/454,016, inventor Sachdeva et al., entitled "NiTiNb Alloy Processing Method and Articles Formed Thereby" (nickel-titanium-niobium-alloy). The disclosures of U.S. Pat. No. 5,044,947 and the aforesaid applications are hereby incorporated by reference.

The specific alloy composition is not critical to the present invention; other materials which exhibit superelastic effects may be used. For example U.S. Pat. No. 5,429,501, herein incorporated in its entirety by reference, discloses superelastic and shape memory beta-phase titanium. To form beta-phase titanium, metallic titanium may be alloyed with molybdenum, chromium, zirconium, tin, vanadium, iron or niobium. Other compositions such as Cu-Zn alloys are also known to be superelastic and are suitable for use in the present invention. Another material suitable for use in the present invention is a work hardened nickel titanium having a martensitic crystal structure, such as that sold under the tradename NITANOL for orthodontic wires by Unitek Corp., Arcadia Calif.

Figure 6:
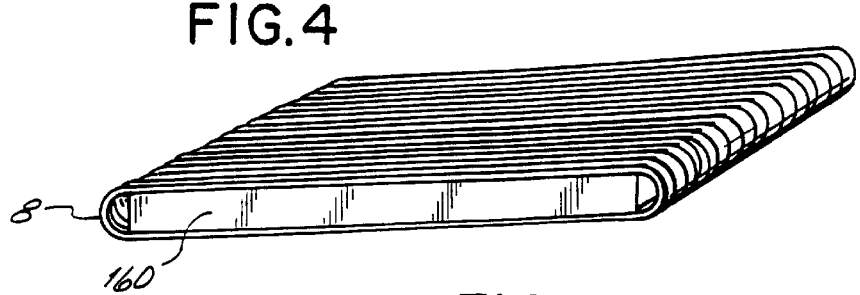
FIG. 6 is a perspective view of the apparatus used in straightening of the superelastic wire.

Superelastic materials have a temperature range in which the material may be permanently deformed. This range is known as the working temperature range Tw. When a superelastic wire is heated to a temperature in the working temperature range Tw, the wire may be permanently deformed so that when the wire is cooled, the deformed shape is maintained. Typically, the superelastic wire is packaged in coils and should be straightened prior to grinding and twisting. One method of straightening the wire 8 is to wrap the wire around a mandrel 160 as shown in FIG. 6. The mandrel 160 is then placed in a furnace and the wire 8 is heated into the Tw. The wire 8 is then cooled, removed from the mandrel and the curved ends are trimmed.

Superelastic alloys, when in the martensitic state (i.e., below the austenitic transformation temperature Af, the temperature at which the material is about 100% austenite), retain their deformed shape when subjected to stress. However the shape memory property returns the deformed material to its original predeformation configuration when heated above Af. In the present invention it is preferred to use an alloy having an Af temperature lower than about 37° C. (body temperature) so that the file will be in the austenitic phase during use in the body.

When the superelastic material is twisted, the material may form a stress induced martensite phase since less energy is necessary to stress induce and deform martensite than to deform austenite. If the file preform is deformed at room temperature and there is not enough strain to induce plastic deformation of the martensite phase, the wire will spring back to its original shape once the twisting force is released. It is also possible to permanently deform superelastic material by heating within the Tw range prior to and during twisting. Another method of permanently deforming a preform is by performing a rapid twist step to heat the superelastic material by internal friction to a temperature at which the material does form a stress induced martensite.

As used herein, the terms shape-memory alloy and superelastic alloy are intended to include all suitable alloy compositions which possess shape-memory and/or superelastic properties, respectively. Moreover, the term superelastic is intended to mean the ability of a material to withstand at least twice as much strain as stainless steel materials can withstand without plastic deformation. The term shape memory is intended to mean the ability of a wire to recover to its original state by the use of temperature. The term rhombus or rhomboidal is intended to define a geometric shape, having four major sides, which is substantially a parallelogram, i.e., including four equal sides and no internal right angles.

Figure 1:
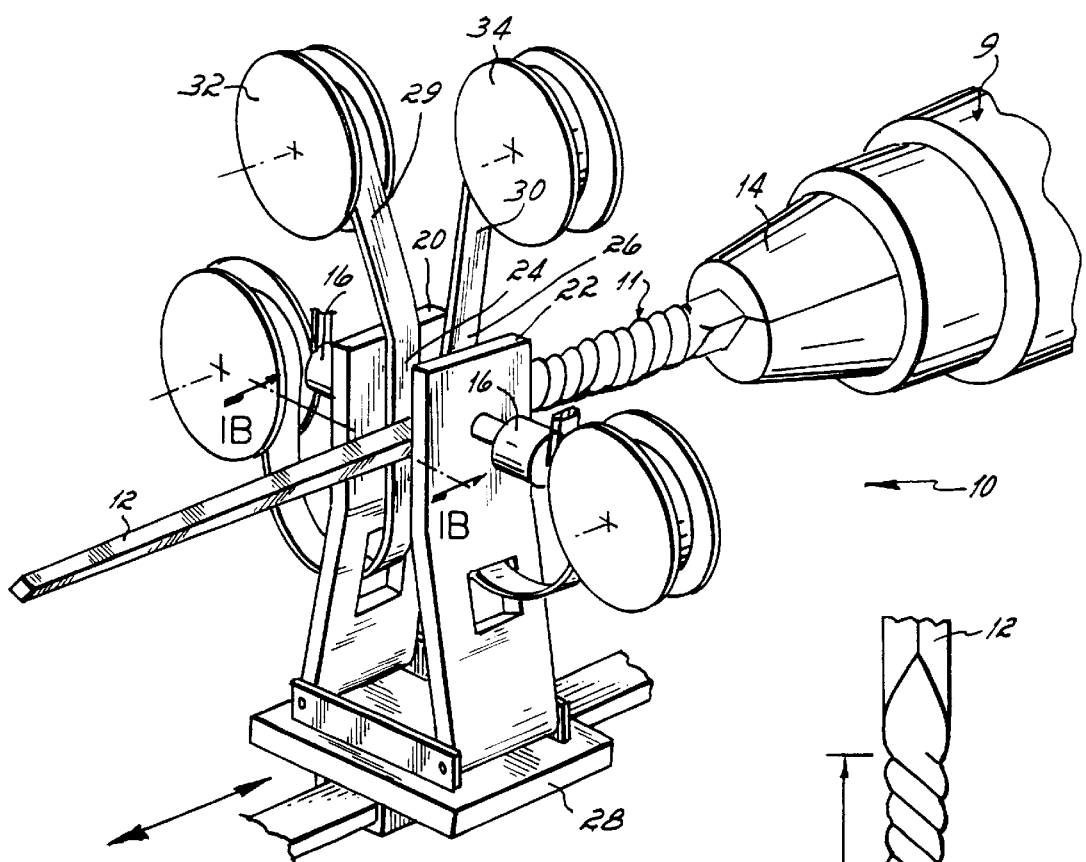
FIG. 1 is a schematic perspective view of one type of apparatus used in fabricating the file of the present invention.
Figure 1B:
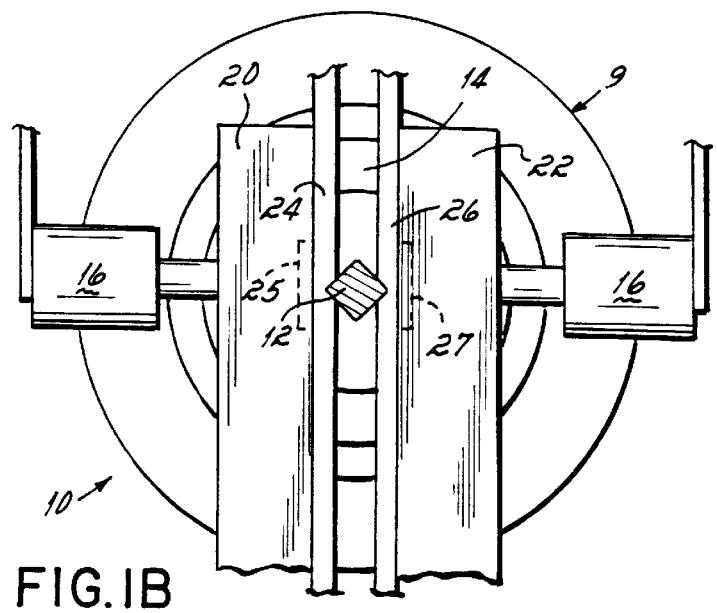
FIG. 1B is an enlarged cross-sectional view taken on line 1B—1B of FIG. 1A.

The files and file-forming processes of this invention are implemented, in preferred embodiments, with the apparatus 10 depicted in FIG. 1. Prior to twisting, file preforms are ground to the desired shape, including: length, transverse cross-section and taper, on any one of the devices shown in FIGS. 2, 3, or 5.

Figure 1A:
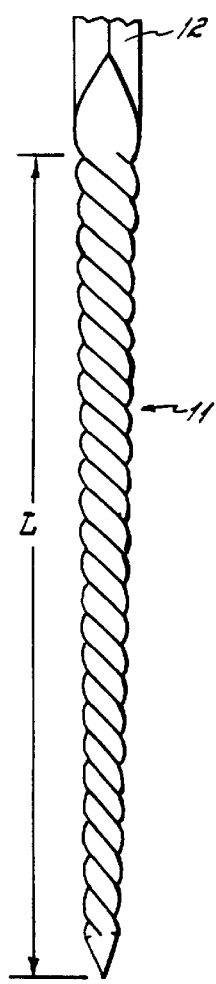
FIG. 1A is a side view of a file formed on the apparatus of FIG. 1.
Figure 2:
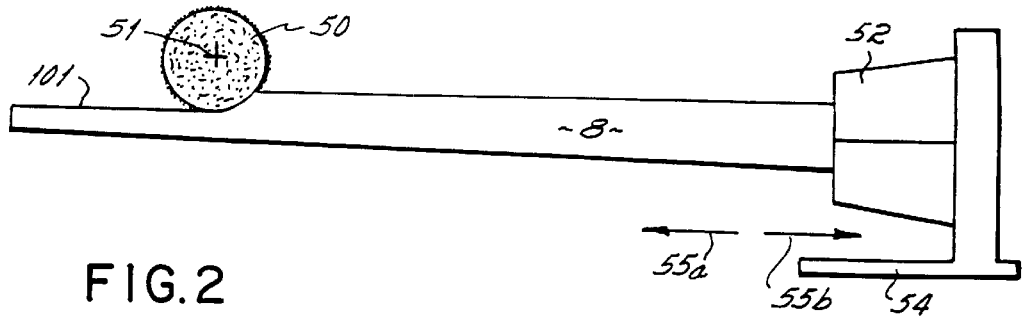
FIG. 2 is a schematic side view of one apparatus for forming a flat surface along the length of a file blank.

Cylindrical superelastic wires 8 are ground to form file preforms 12 which are subsequently twisted to form helically fluted files 11. The cylindrical rod 8 is mounted into collet 52 which is fixedly mounted upon a stage 54 which is selectively horizontally movable in opposite directions as designated by arrows 55a and 55b. Once rod 8 is mounted in the collet 52, grinding wheel 50 is lowered into contact with the rod 8. Stage 54 is then advanced horizontally rightwardly, as is seen in FIG. 2, to move collet 52 and rod 8 axially so that a flat surface 101 is ground on one side of the rod 8. After one such flat, that is, flat surface, has been ground along the working length L (see FIG. 1A) of the rod, grinding wheel 50 is lifted vertically, and stage 54 is moved axially leftwardly to the initial or home position so that the grinding wheel 50 is aligned with the upper portion of the inner end of the working length of the partially ground rod. Collet 52 is then indexed about its central axis by a predetermined angle, the magnitude of which depends on the number of flutes desired in the finished file. Indexing rotational angles of 180°, 120° and 90° are employed for 2, 3 and 4 flute files, respectively. It is also possible to rotate the collet by a series of angles (e.g. 60°, 120°, 60°) to obtain a file preform having a rhomboidal cross section. Grinding wheel 50 is then lowered to the desired depth of contact with the rod 8, and stage 54 is then moved rightwardly to move rod 8 axially past grinding wheel 50 to grind the second flat surface on the file blank. The foregoing process is repeated until all the flats have been ground on the file blank.

Figure 2A:
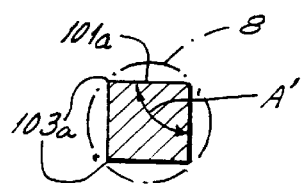
FIGS. 2A, 2B, 2C and 2D are transverse cross-sectional views, perpendicular to the longitudinal axis of the finished file or the file blank using the apparatus of FIG. 2 or FIG. 6.
Figure 2B:
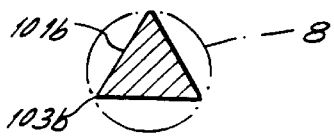
Figure 2C:
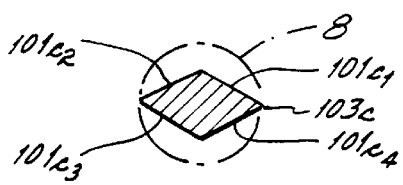

As noted, by varying the angle which collet 52 indexes rod 8, it is possible to form file blanks having three or more apices 103 shown generally in FIGS. 2A–2C. The apices 103 of the preground file blank, once twisted, and permanently helically fluted, form the cutting edges of the helically fluted file. Typically, files include three or four apices or helical cutting edges 103.

Figure 2D:
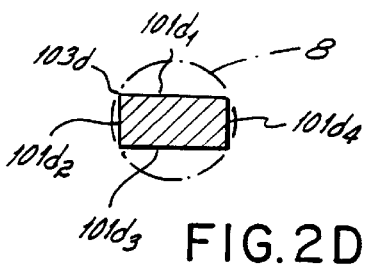

In order to form a file blank having a square transverse cross section as shown in FIG. 2A, rod 8 is indexed 90° after each flat surface 101 is ground. In order to form a file blank having three apices and a triangular transverse cross section, the rod is indexed 120° after each flat surface is formed (as shown in FIG. 2B). Using the method of the present invention it is also possible to form a file having a rhomboidal transverse cross section (FIG. 2C). This is accomplished by grinding a first flat surface 101C$_1$; indexing the rod 60° clockwise as viewed in FIG. 2C and grinding a second flat surface 101C$_2$; indexing the rod 120° clockwise as viewed in FIG. 2C and grinding a third flat surface 101C$_3$; and indexing the rod 60° clockwise as viewed in FIG. 2C and grinding the fourth flat surface 101C$_4$. It is not necessary to change the initial depth of cut of the wheel to fabricate the square, triangular and rhomboidal preforms shown in FIGS. 2A–2C, respectively. However, in order to fabricate a preform having a rectangular cross-section, as shown in FIG. 2D, the initial depth of cut may be adjusted prior to forming each flat side or may be adjusted after opposing pairs of edges are ground. For example, as seen in FIG. 2D, a first flat side 101d$_1$, is ground; the rod 8 is then indexed 90°, the initial depth of cut reduced and a second flat side 101d$_2$ is ground; rod 8 is then indexed 90°, the initial depth of cut is increased to the depth used for the cut of side 101d$_1$ and a third flat side 101d$_3$ is ground; rod 8 is then indexed 90°, the initial depth of cut is reduced to the depth used for the cut of side $101d_2$ and fourth side $101d_4$ is ground. It is also possible to grind flat side $101d_1$, index the rod 180°, and grind flat side $101d_4$; index the rod 90° and decrease the initial depth of cut and grind flat side $101d_2$; and finally index the rod 180° and grinding the final flat side $101d_3$.

Figure 3:
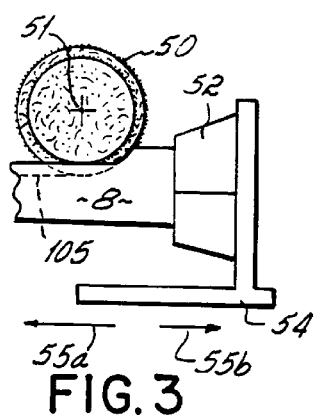
FIG. 3 is a schematic side view of an apparatus similar to FIG. 2 for forming a concave surface along the length of a file blank.
Figures 3A, 3B:
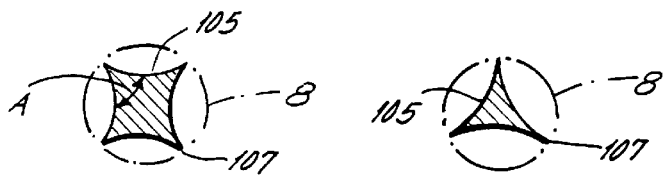
FIGS. 3A, 3B and 3C are transverse cross-sectional views, perpendicular to the longitudinal axis of the finished file or the file blank, showing concave surfaces formed on file blanks, using the apparatus of FIG. 3.
Figure 3C:
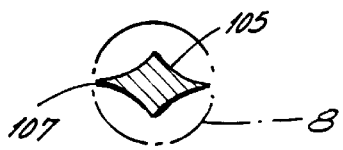

It is possible to form a variety of different cross sectional shapes by varying the surface of the grinding wheel and/or the index angles. For example, by dressing the surface of grinding wheel 50 so that the surface is convexed, as shown in FIG. 3, it is possible to form ground surfaces 105 having the concave shapes shown in FIGS. 3A, 3B and 3C, rather than the flat shapes of the surfaces 101 shown in FIGS. 2A, 2B and 2C. When the surface of the grinding wheel 50 is convexed, the angle A of the apices 107 (FIG. 3A) is more acute for a file having the same index angle and number of sides than is angle A' of the apices 103 (FIG. 2A) when the surface of the grinding wheel 50 is flat (FIG. 2). While angle A is more acute and provides a sharper cutting edge, that edge is weaker due to the lower amount of material at the apex. Thus, the apices shown in FIGS. 2A–2C are more rugged to maintain a usable edge and provide for a longer working life.

Figure 5:
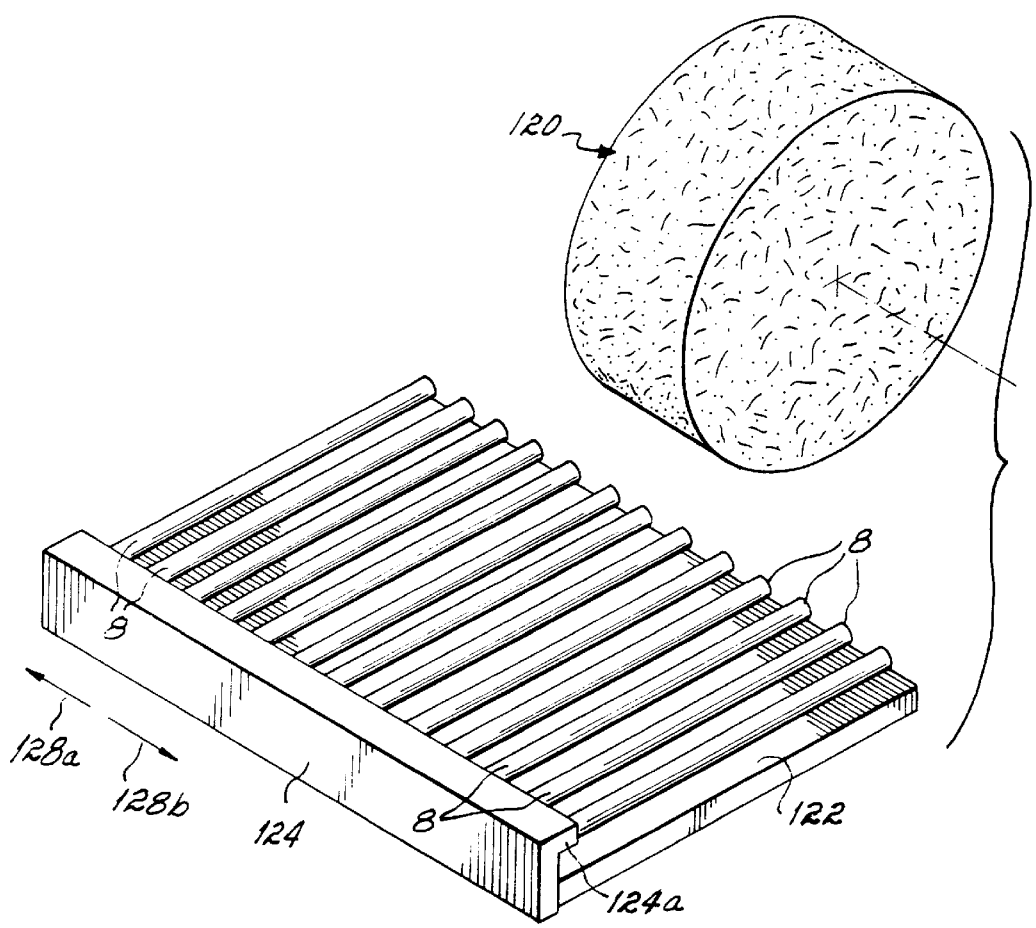
FIG. 5 is a perspective view of another apparatus for forming flat surfaces along the length of a number of file blanks.
Figure 4:
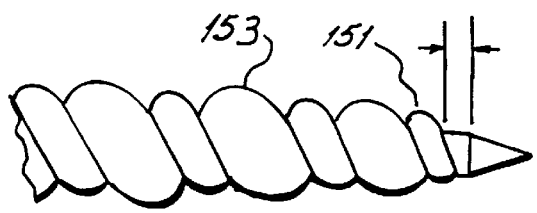
FIG. 4 is a detail view of a rhomboidal file tip.

Another device for grinding cylindrical rods 8 is shown in FIG. 5. FIG. 5 shows a wide grinding wheel 120 which moves transversely to the longitudinal axes of a large number of rods 8 to grind a flat surface onto the rods. The cylindrical rods 8 are placed upon rest 122. The rods 8 are disposed in parallel and extend along substantially the entire width of the rest 122. The parallel rods 8 are held by retainer 124 which is movable along the length of rest 122 as shown by opposing arrows 128a and 128b. Movable retainer 124 includes lateral projection 124a which extends over an end portion of rods 8 to secure the rods to rest 122 and prevent the rotation of the rods during grinding. Once rods 8 are retained between the lateral projection 124a and the rest 122, grinding wheel 120 moves back and forth across the width of rest 122 to grind a flat surface on the entire working length of each rod 8. Typically, the grinding 120 wheel moves across each rod twice, once while traveling away from projection 124a and once while traveling toward projection 124a. During grinding, the wheel 120 may be moved straight across the rods or may move in a figure eight or zigzag pattern. The grinding wheel is preferably a porous wheel such as an ANSI standard C-60IV wheel rotating at a rate between 3,000 and 8,000 surface feet per minute and preferably about 5,000 surface feet per minute. The material is passed under the wheel at a feed rate between about 50 and 100 lineal feet per minute, and preferably about 75 lineal feet per minute.

After grinding a first flat side, the movable retainers 124 is translated with respect to the rest 122. The lateral projection 124a of the retainers 124 remains in contact with rods 8 so that the movement of the retainer along the direction shown by arrows 128a, 128b causes each rod to rotate by a predetermined angle about the longitudinal axis of the rods 8. Once the rotation is complete, a second flat surface is ground across the working length of the rod. Depending upon the desired cross section of the file 11, the rods 8 are typically rotated and ground one or more times.

After the file blanks have been ground to the desired cross-sectional file preform shape they are preferably heated to a temperature above ambient temperature prior to, during and subsequent to the twisting operation using thermal or frictional energy or a combination thereof. This temperature can be as high as the working temperature range Tw of the material of which they are formed.

The heating process may externally heat the wire preform in the collet 14 by the provision of induction coils, radiant heating elements or electrodes to provide for joulian heating. The temperature to which the preform is heated is based upon the specific alloy used. Alternatively, the files can be heated without the application of heat from an external heat source by twisting rapidly so that internal friction heats the file.

Once the file preforms are formed, they are twisted or heated and twisted on a device such as that shown in FIG. 1. The twisting apparatus 10, shown in FIG. 1, includes a drive head 9 which rotates about a horizontal axis. Extending from the drive head 9 is a collet 14 which circumferentially grips and secures the proximal or inner end of a preformed ground file blank 12 for rotation about the longitudinal axis thereof. The distal or outer end portion of the file blank 12 is secured by opposing jaws 20, 22, which are mounted on a stage 28 which moves parallel to the longitudinal axis of the file blank (horizontally as shown in FIG. 1), away from collet 14 at a predetermined rate as the collet rotates to twist the file blank 12. At least one of the jaws includes a spring or air cylinder 16 so that it may be compressed against the opposing jaw with a constant force. Each jaw includes a protectant layer 24, 26 which is malleable and able to withstand the working temperature of the file blank 12. Brass is one material known to be suitable. With each subsequent file formed, the jaws 20, 22 are provided with a new protectant layer 20 24, 26 from strips 29, 30 from a source 32, 34 such as take-off reels. The protectant layer may optionally be contacted by a heating element 25, 27 which may heat by any suitable process, such as an electrical heating process of joulian, radiant or induction heating or may be supplied with a heated fluid such as steam or oil.

In order to optimize the superelastic properties of the finished file it is desirable, although not essential, to heat treat the twisted files. The heat treatment may be performed in any furnace with air circulation. The radiant heating elements or electrodes to provide for joulian heating can be used for the post twist heat treatment.

Typically the files are made in a variety of working lengths varying from 19–30 mm. The specific variables which are typically controlled in fabricating such files are set forth in the Tables 1 and 2. In Tables 1 and 2 the variables A and B represent the minimum thickness of the transverse cross section at 16.00 mm and 3.00 mm, respectively, from the tip. The variables C and D represent the maximum thickness of the transverse cross section at 16.00 mm and 3.00 mm, respectively, from the tip.

Table 1 describes the characteristics of a twisted rhomboidal file. In observing the longitudinal cross section of a rhomboidal file there are alternating large flutes 153, resulting from the major axis of the rhombus, and small flutes 151, resulting from the minor axis of the rhombus. In Table 1 the column entitled Tight Flute Limit includes two values. The first value is the minimum acceptable length of a small flute 151 resulting from the twisting of the minor axis of the rhombus. The second value is the minimum acceptable length of a large flute 153 resulting from the twisting of the major axis of the rhombus. Similarly, the column entitled Loose Flute Limit includes two values. The first value is the maximum acceptable length of a small flute 151 resulting from the twisting of the minor axis of the rhombus. The second value is the maximum acceptable length of a large flute 153 resulting from the twisting of the major axis of the rhombus. In Table 1 the column labeled T max represents the maximum acceptable length of the untwisted portion at the distal tip of the file. In Table 2 the value L is the length of the ground portion of the rod.

TABLE 1

| Size | Wire Dia. (Inches) | No. of Twists | No. of Edges ±1 | Tight Flute Limit (mm) | Loose Flute Limit (mm) | A (mm) | B (mm) | T Max. (mm) |
|---|---|---|---|---|---|---|---|---|
| 40  | .035 | 7    | 28 | 0.368/0.500 | 0.673/0.813 | 0.720 | 0.460 | 0.25 |
| 45  | .035 | 6.5  | 26 | 0.406/0.622 | 0.711/0.927 | 0.770 | 0.510 | 0.34 |
| 50  | .037 | 6.25 | 25 | 0.394/0.660 | 0.699/0.965 | 0.820 | 0.560 | 0.38 |
| 55  | .041 | 6    | 24 | 0.381/0.660 | 0.686/0.965 | 0.870 | 0.610 | 0.38 |
| 60  | .041 | 5.75 | 23 | 0.406/0.787 | 0.711/1.092 | 0.920 | 0.660 | 0.38 |
| 70  | .048 | 5.5  | 22 | 0.279/0.838 | 0.813/1.372 | 1.020 | 0.760 | 0.38 |
| 80  | .051 | 5.25 | 21 | 0.292/0.851 | 0.826/1.384 | 1.120 | 0.860 | 0.38 |
| 90  | .055 | 4.75 | 19 | 0.292/0.851 | 0.927/1.473 | 1.220 | 0.960 | 0.38 |
| 100 | .063 | 4    | 16 | 0.318/1.016 | 0.927/1.626 | 1.320 | 1.060 | 0.38 |
| 110 | .063 | 3.75 | 15 | 0.381/1.088 | 1.092/1.788 | 1.420 | 0.160 | 0.38 |
| 120 | .069 | 3.5  | 14 | 0.434/1.194 | 1.146/1.905 | 1.520 | 1.260 | 0.38 |
| 130 | .076 | 3.25 | 13 | 0.470/1.222 | 1.181/1.933 | 1.620 | 1.360 | 0.38 |
| 140 | .076 | 3    | 12 | 0.518/1.283 | 1.232/1.994 | 1.720 | 1.460 | 0.38 |

TABLE 2

| Size | Sides | Rod Diameter (mm) | A (mm) | B (mm) | L (mm) | C (mm) | D (mm) |
|---|---|---|---|---|---|---|---|
| 08  | 4 | 0.51 | 0.305–0.279 | 0.122–0.096 | 20.98–19.81 |             |             |
| 10  | 4 | 0.51 | 0.323–0.297 | 0.132–0.107 | 20.98–19.81 |             |             |
| 15  | 4 | 0.56 | 0.356–0.330 | 0.170–0.145 | 20.98–19.81 |             |             |
| 20  | 4 | 0.61 | 0.394–0.368 | 0.208–0.183 | 20.98–19.81 | .290–.278   | .551–.526   |
| 25  | 4 | 0.66 | 0.437–0.411 | 0.244–0.218 | 20.98–19.81 | .340–.315   | .612–.587   |
| 30  | 4 | 0.71 | 0.470–0.455 | 0.279–0.254 | 20.98–19.81 | .389–.363   | .660–.635   |
| 35  | 4 | 0.79 | 0.503–0.478 | 0.312–0.287 | 21.34–20.32 | .437–.411   | .706–.681   |
| 40  | 4 | 0.79 | 0.533–0.508 | 0.356–0.330 | 21.34–20.32 | .498–.427   | .765–.739   |
| 45  | 4 | 0.89 | 0.577–0.551 | 0.386–0.361 | 21.59–20.32 | .541–.516   | .810–.785   |
| 50  | 4 | 0.94 | 0.622–0.597 | 0.422–0.396 | 21.59–20.32 | .589–.564   | .874–.848   |
| 55  | 4 | 0.94 | 0.655–0.630 | 0.462–0.437 | 21.59–20.32 | .648–.622   | .922–.897   |
| 60  | 4 | 1.04 | 0.701–0.676 | 0.495–0.470 | 22.35–20.98 | .696–.671   | .986–.960   |
| 70  | 4 | 1.12 | 0.767–0.727 | 0.574–0.528 | 22.35–20.98 | .800–.760   | 1.077–1.036 |
| 80  | 4 | 1.22 | 0.858–0.818 | 0.655–0.610 | 22.35–20.98 | .922–.881   | 1.207–1.166 |
| 90  | 4 | 1.40 | 0.945–0.895 | 0.731–0.691 | 23.01–20.98 | 1.019–.978  | 1.314–1.273 |
| 100 | 4 | 1.60 | 0.993–0.953 | 0.795–0.755 | 24.38–23.01 | 1.109–1.069 | 1.395–1.354 |
| 110 | 4 | 1.60 | 1.151–1.111 | 0.940–0.900 | 24.89–23.62 | 1.311–1.270 | 1.617–1.577 |
| 120 | 4 | 1.75 | 1.214–1.174 | 0.998–0.958 | 24.89–23.62 | 1.393–1.351 | 1.706–1.666 |
| 130 | 4 | 1.93 | 1.299–1.258 | 1.082–1.042 | 24.89–23.62 | 1.510–1.469 | 1.824–1.783 |
| 140 | 4 | 1.93 | 1.384–1.344 | 1.151–1.111 | 24.89–23.62 | 1.606–1.565 | 1.945–1.905 |

It will be appreciated that different alloy compositions will possess a different shape-memory characteristic, a different transformation temperature (Af), a different modulus of elasticity, and a different working temperature range Tw. It is within the skill of one in the art based upon the teachings of the present invention to adjust the heating, twisting and heat treating steps based upon the specific properties of the material used.

While the present invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details, representative apparatus and method as shown and described. This has been a description of the present invention, along with the preferred method of practicing the present invention as currently known. However, the invention itself should only be defined by the appended claims, wherein

We claim:

1. A superelastic endodontic appliance formed by substantial plastic deformation of a preformed blank comprising the steps of:

providing a preform having a predetermined cross section and formed of a superelastic material;

twisting the preform about the longitudinal axis to form an appliance having helically shaped edges; and maintaining the preform in the austenite phase until the twisting step.

2. The superelastic article of claim 1 wherein the material of the file transforms to martensitic phase during the twisting step.

3. The superelastic article of claim 1 wherein the material is a Ti alloy.

4. The superelastic file of claim 3 wherein said material is selected from the group consisting of stoichiometric NiTi, near-equiatomic Ni-Ti, Ni-Ti-Nb alloys, Ni-Ti-Fe alloys, Ni-Ti-Cu alloys, beta-phase titanium alloys and combinations thereof.

5. The superelastic file of claim 3 wherein said material is at least about 40 atomic percent Ti.

6. The superelastic appliance of claim 1 wherein said appliance is selected from the group consisting of files and reamers.

7. The superelastic appliance of claim 1 wherein the maintaining step includes external heating of the preform.

8. The superelastic appliance of claim 1 wherein the maintaining step includes heating of the preform by internal friction during twisting.

9. A superelastic endodontic appliance formed by substantial plastic deformation of a preformed blank comprising the steps of:
provyding a preform having a predetermined cross section and formed of a superelastic material;
twisting the preform about the longitudinal axis to form an appliance having helically shaped edges; and
heating the preform to the austenite phase until twisting.

10. The superelastic article of claim 9 wherein the material of the file transforms to martensitic phase following the twisting step.

11. The superelastic article of claim 9 wherein the material is a Ti alloy.

12. The superelastic file of claim 11 wherein said material is selected from the group consisting of stoichiometric NiTi, near-equiatomic Ni-Ti, Ni-Ti-Nb alloys, Ni-Ti-Fe alloys, Ni-Ti-Cu alloys, beta-phase titanium alloys and combinations thereof.

13. The superelastic file of claim 11 wherein said material is at least about 40 atomic percent Ti.

14. The superelastic appliance of claim 9 wherein said appliance is selected from the group consisting of files and reamers.

15. The superelastic appliance of claim 9 wherein the heating step includes external heating of the preform.

16. The superelastic appliance of claim 9 wherein the heating step includes heating of the preform by internal friction during twisting.

17. A superelastic endodontic file comprising a shaft having a working length;
at least three cutting apices with adjacent cutting apices defining surfaces therebetween, said apices being permanently helically deformed about the working length of said shaft to form helically shaped cutting edges; and
the surfaces of the shaft between adjacent longitudinal cutting edges defining elongated helical surfaces which are flat when viewed in transverse cross section.

18. A superelastic endodontic file comprising a shaft comprising:
a handle section at its proximal end and a tip at its distal end a working length therebetween;
four or more cutting apices helically arranged about said shaft; and
wherein the working length of said shaft has a transverse cross-sectional area which is substantially rhomboidal along its length.

19. The file of claim 18 wherein the working length is tapered such that the rhomboidal cross-section decreases in area toward the tip.

20. An endodontic file having cutting edges formed at the apices of a predetermined transverse cross-sectional shape, comprising:
a working length portion, formed of a material exhibiting super-elasticity, having a predetermined transverse cross sectional area, and one or more apices defining cutting edges along the length thereof,
said working length being permanently plastically deformed about its longitudinal axis to form said cutting edges at the apices thereof.

21. The endodontic file of claim 20 wherein said working length includes at least three cutting apices helically arranged about the working length of said shaft.

22. The endodontic file of claim 20 further comprising:
helical surfaces arranged between adjacent cutting apices which are substantially flat when viewed in transverse cross section.

23. The endodontic file of claim 20 wherein said working length includes at least four cutting apices helically arranged about the working length of said shaft.

24. The endodontic file of claim 23 further comprising: a flat side arranged between adjacent cutting apices.

25. The superelastic file of claim 20 wherein said material is selected from the group consisting of near-equiatomic Ni-Ti, Ni-Ti-Nb alloys, Ni-Ti-Fe alloys, Ni-Ti-Cu alloys, Ni-Ti-Nb alloys and beta-phase titanium.

26. The superelastic file of claim 20 wherein said material is at least about 40 atomic percent Ti.

27. The superelastic file of claim 26 wherein said material is about 50.8 atomic percent Ti and about 49.2 atomic percent Ni.

28. The superelastic file of claim 20 wherein said predetermined transverse cross-sectional shape is selected from the group consisting of three and four sided polygons.

29. The superelastic file of claim 20 wherein said predetermined transverse cross-sectional shape is substantially rhomboidal.

30. The superelastic file of claim 29 wherein said rhombus has angles of about 60°–120°–60°–120°.

* * * * *

UNITED STATES PATENT AND TRADEMARK OFFICE
CERTIFICATE OF CORRECTION

PATENT NO.    : 6,315,558 B1
DATED         : November 13, 2001
INVENTOR(S)   : Farzin-Nia et al.

It is certified that error appears in the above-identified patent and that said Letters Patent is hereby corrected as shown below:

Column 6,
Line 28, reads ". . .with a new protectant layer 20 24, 26 from. . ." and should read -- . . .with a new protectant layer 24, 26 from. . . --.

Column 7,
Line 15, TABLE 1 reads "0.160" and should read -- 1.160 --.

Column 7, lines 65-67 through Column 8, lines 1,2, 45-48,
Claim 1 reads "A superelastic endodontic appliance formed by substantial plastic deformation of a preformed blank comprising the steps of:
    providing a preform having a predetermined cross section and formed of a superelastic material;
    twisting the preform about the longitudinal axis to form an appliance having helically shaped edges; and
    maintaining the preform in the austenite phase until the twisting step" and should read -- A superelastic endodontic appliance formed by a method involving plastic deformation of a preformed blank, the method comprising:
    providing a preformed blank having a predetermined cross section and a longitudinal axis, and formed of a superelastic material;
    twisting the preformed blank about the longitudinal axis to form an appliance having helically shaped edges; and
    maintaining the preformed blank in the austenite phase of the superelastic material until the twisting step --.

Column 8,
Lines 49-51, Claim 2, reads, "the superelastic article of claim 1 wherein the material of the file transforms to martensitic phase during the twisting step" and should read -- The superelastic endodontic appliance of claim 1 wherein the material of the file transforms to martensitic phase during the twisting step --.

Lines 52-53, Claim 3, reads, "The superelastic article of claim 1 wherein the material is a Ti alloy" and should read -- The superelastic endodontic appliance of claim 1 wherein the material is a Ti alloy --.

UNITED STATES PATENT AND TRADEMARK OFFICE
CERTIFICATE OF CORRECTION

PATENT NO.    : 6,315,558 B1
DATED         : November 13, 2001
INVENTOR(S)   : Farzin-Nia et al.

It is certified that error appears in the above-identified patent and that said Letters Patent is hereby corrected as shown below:

Column 8, cont'd,
Lines 54-58, Claim 4, reads "The superelastic file of claim 3 wherein said material is selected from the group consisting of stoichiometric NiTi, near-equiatomic Ni-Ti, Ni-Ti-Nb alloys, Ni-Ti-Fe alloys, Ni-Ti-Cu alloys, beta-phase titanium alloys and combinations thereof' and should read -- The superelastic endodontic appliance of Claim 3, wherein said material is selected from the group consisting of stoichiometric NiTi, near equiatomic Ni-Ti, Ni-Ti-Nb alloys, Ni-Ti-Fe alloys, Ni-Ti-Cu alloys, beta-phase titanium alloys and combinations thereof --.

Lines 59-60, Claim 5, reads, "The superelastic file of claim 3 wherein said material is at least about 40 atomic percent Ti" and should read -- The superelastic endodontic appliance of claim 3 wherein said material is at least about 40 atomic percent Ti --

Lines 61-63, Claim 6, reads, "The superelastic appliance of claim 1 wherein said appliance is selected from the group consisting of files and reamers" and should read -- The superelastic endodontic appliance of claim 1 wherein said appliance is selected from the group consisting of files and reamers --.

Lines 64-65, Claim 7, reads, "The superelastic appliance of claim 1 wherein the maintaining step includes external heating of the preform" and should read -- The superelastic endodontic appliance of claim 1 wherein the maintaining step includes external heating of the preformed blank --.

Lines 63-68, Claim 8, reads, "The superelastic appliance of claim 1 wherein the maintaining step includes heating of the prefom by internal friction during twisting" and should read -- The superelastic endodontic appliance of claim 1 wherein the maintaining step includes heating the preformed blank by internal friction during twisting --.

Column 9,
Claim 9 reads, "A superelastic endodontic appliance formed by substantial plastic deformation of a preformed blank comprising the steps of:
    providing a preform having a predetermined cross section and
formed of a superelastic material;

UNITED STATES PATENT AND TRADEMARK OFFICE
CERTIFICATE OF CORRECTION

PATENT NO. : 6,315,558 B1
DATED : November 13, 2001
INVENTOR(S) : Farzin-Nia et al.

It is certified that error appears in the above-identified patent and that said Letters Patent is hereby corrected as shown below:

<u>Column 9, cont'd,</u>
twisting the preform about the longitudinal axis to form an appliance having helically shaped edges; and
heating the preform to the austenite phase until twisting" and should read -- A superelastic endodontic appliance formed by a method of substantial plastic deformation of a preformed blank, the method comprising:
providing a preformed blank having a predetermined cross section and a longitudinal axis, and formed of a superelastic material;
twisting the preformed blank about the longitudinal axis to form an appliance having helically shaped edges; and heating the preformed blank to the austenite phase until twisting --.

Lines 9-11, Claim 10 reads, "The superelastic article of claim 9 wherein the material of the file transforms to martensitic phase following the twisting step" and should read -- The superelastic endodontic appliance of claim 9 wherein the superelastic material transforms to martensitic phase following the twisting step --.

Lines 12-13, Claim 11 reads, "superelastic article" and should read -- superelastic endodontic appliance --.

Lines 14-18, Claim 12 reads, "superelastic file" and should read -- superelastic endodontic appliance --.

Lines 19-20, Claim 13 reads, "superelastic file" and should read -superelastic endodontic appliance --.

Lines 21-23, Claim 14 reads, "superelastic appliance" and should read -- superelastic endodontic appliance --.

UNITED STATES PATENT AND TRADEMARK OFFICE
CERTIFICATE OF CORRECTION

PATENT NO. : 6,315,558 B1
DATED : November 13, 2001
INVENTOR(S) : Farzin-Nia et al.

It is certified that error appears in the above-identified patent and that said Letters Patent is hereby corrected as shown below:

Column 9, cont'd,
Lines 24-25, Claim 15 reads, "The superelastic appliance of claim 9 wherein the heating step includes external heating of the preform" and should read -- The superelastic endodontic appliance of claim 9 wherein the heating step includes external heating of the preformed blank --.

Lines 26-28, Claim 16 reads, "The superelastic appliance of claim 9 wherein the heating step includes heating of the preform by internal friction during twisting" and should read -- The superelastic endodontic appliance of claim 9 wherein the heating step includes heating of the preformed blank by internal friction during twisting --

Lines 39-47, Claim 18 reads, "A superelastic endodontic file comprising a shaft comprising:
    a handle section at its proximal end and a tip at its distal end a working length therebetween;
    four or more cutting apices helically arranged about said shaft; and
    wherein the working length of said shaft has a transverse cross-sectional area which is substantially rhomboidal along its length" and should read -- A superelastic endodontic file comprising:
    a shaft having proximal and distal ends;
    a handle section at said proximal end and a tip at said distal end and a working length therebetween; and
    four or more cutting apices helically arranged about said shaft;
    wherein the working length of said shaft has a transverse cross-sectional area which is substantially rhomboidal along its length --.

Column 10,
Lines 4-15, Claim 20 reads, "An endodontic file having cutting edges formed at the apices of a predetermined transverse cross-sectional shape, comprising:
    a working length portion, formed of a material exhibiting super-elasticity, having a predetermined transverse cross sectional area, and one or more apices defining cutting edges along the length thereof,

UNITED STATES PATENT AND TRADEMARK OFFICE
CERTIFICATE OF CORRECTION

PATENT NO. : 6,315,558 B1
DATED : November 13, 2001
INVENTOR(S) : Farzin-Nia et al.

It is certified that error appears in the above-identified patent and that said Letters Patent is hereby corrected as shown below:

Column 10, cont'd,
said working length being permanently plastically deformed about its longitudinal axis to form said cutting edges at the apices thereof." and should read
-- An endodontic file comprising:
a working length portion having a longitudinal axis and formed of a material exhibiting super-elasticity, said working length portion further having a predetermined transverse cross- sectional area and at least one apex defining a cutting edge along the working length portion,
said working length portion being permanently plastically deformed about its longitudinal axis to form said cutting edge at the apex thereof. --.

Lines 16-18, Claim 21 reads, "The endodontic file of claim 81 wherein said working length includes at least three cutting apices helically arranged about the working length of said shaft" and should read -- The endodontic file of claim 81 wherein said working length includes at least three of said apices and cutting edges helically arranged about the working length of said shaft. --.

Lines 19-23, Claim 22 reads, "The endodontic file of claim 20 further comprising:
helical surfaces arranged between adjacent cutting apices which are substantially flat when viewed in transverse cross section." and should read -- The endodontic file of claim 21 further comprising:
helical surfaces arranged between adjacent cutting edges apices which are substantially flat when viewed in transverse cross section. --.

Lines 24-26, Claim 23 reads, "The endodontic file of claim 20 wherein said working length includes at least four cutting apices helically arranged about the working length of said shaft" and should read -- The endodontic file of claim 20 wherein said working length portion includes at least four of said apices and said cutting edges helically arranged about the working length portion --.

Line 28, "apices" should read -- edges --.
Lines 29 and 33, "superelastic" should read -- endodontic --.

UNITED STATES PATENT AND TRADEMARK OFFICE
CERTIFICATE OF CORRECTION

PATENT NO.   : 6,315,558 B1
DATED        : November 13, 2001
INVENTOR(S)  : Farzin-Nia et al.

It is certified that error appears in the above-identified patent and that said Letters Patent is hereby corrected as shown below:

Column 10,
Lines 35, 38 and 41, "superelastic" should read -- endodontic --.

Lines 44-45, Claim 30 reads, "The superelastic file of claim 90 wherein said rhombus has angles of about 60°-120°-60°-120°" and should read -- The endodontic file of claim 90 wherein said rhomboidal shape has angles of about 60°-120°-60°-120° --.

Signed and Sealed this

Sixth Day of May, 2003

JAMES E. ROGAN
*Director of the United States Patent and Trademark Office*